United States Patent
Parks et al.

(10) Patent No.: US 8,901,091 B2
(45) Date of Patent: Dec. 2, 2014

(54) METHOD OF TREATING HERPES VIRUS INFECTION USING MACROCYCLIC LACTONE COMPOUND

(75) Inventors: L. Dean Parks, Ocala, FL (US); Jeffrey D. Parks, Ormond Beach, FL (US)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 13/823,387

(22) PCT Filed: Oct. 14, 2011

(86) PCT No.: PCT/US2011/056351
§ 371 (c)(1),
(2), (4) Date: Mar. 14, 2013

(87) PCT Pub. No.: WO2012/054334
PCT Pub. Date: Apr. 26, 2012

(65) Prior Publication Data
US 2013/0172282 A1    Jul. 4, 2013

Related U.S. Application Data

(60) Provisional application No. 61/394,931, filed on Oct. 20, 2010.

(51) Int. Cl.
*A61K 31/70* (2006.01)
*A61K 31/7048* (2006.01)
*A61K 31/35* (2006.01)
*A61K 31/365* (2006.01)

(52) U.S. Cl.
CPC ............. *A61K 31/7048* (2013.01); *A61K 31/35* (2013.01); *A61K 31/365* (2013.01)
USPC ........................................................ 514/30

(58) Field of Classification Search
CPC ................................................. A61K 31/7048
See application file for complete search history.

(56) References Cited

U.S. PATENT DOCUMENTS

| 6,159,932 | A | 12/2000 | Mencke et al. |
| 2002/0091097 | A1 | 7/2002 | Bratzler et al. |
| 2003/0108596 | A1 | 6/2003 | Sung |
| 2004/0053880 | A1 | 3/2004 | Krieg |

OTHER PUBLICATIONS

Supplemental European Search Report of counterpart European Application No. 11834902.6.
Fatahzadeh et al., "Human Herpes Simplex Virus Infections: Epidemiology, Pathogenesis, Symptomatology, Diagnosis, and Management", Journal of the American Academy of Dermatology, vol. 57, No. 5, Oct. 2007, pp. 737-763 p. 749, col. 1, paragraph 2-p. 755, col. 2, paragraph 3; tables III, IV.
Pavan-Langston, "Herpes Zoster", Ophthalmology, vol. 115, No. 2, Jan. 2008, pp. S13-S20 Abstract; pp. s13, col. 2, paragraph 3-p. s15, col. 2, paragraph 3.
Meinking et al, "The Treatment of Scabies With Ivermectin", New England Journal of Medicine, vol. 333, No. 1, 1995, pp. 26-30 Abstract.
Shoop et al., "Structure and Activity of Avermectins and Milbemycins in Animal Health", Veterinary Parasitology, vol. 59, No. 2, Sep. 1995, pp. 139-156 The whole document.
International Search Report and Written Opinion of International Search Authority of PCT/US2011/056351.

*Primary Examiner* — Elli Peselev
(74) *Attorney, Agent, or Firm* — CUSPA Technology Law Associates, P.A.; Yi Li

(57) ABSTRACT

A method of treating herpes simplex virus infection or varicella zoster virus infection is disclosed. The method includes topically applying a composition containing an effective amount of one or more macrocyclic lactone compounds, including avermectin compounds or milbemycin compounds and a pharmaceutically acceptable carrier to the affected area of an individual suffering from herpes simplex virus infection or varicella zoster virus infection.

23 Claims, No Drawings

METHOD OF TREATING HERPES VIRUS INFECTION USING MACROCYCLIC LACTONE COMPOUND

FIELD OF THE INVENTION

The present invention relates to a method of treating herpes simplex virus and varicella zoster virus infections, more particularly a method of treating herpes simplex virus and varicella zoster virus infections using one or more macrocyclic lactone compounds, more specifically, one or more avermectin compounds or milbemycin compounds.

BACKGROUND OF THE INVENTION

Herpes simplex is a viral disease caused by herpes simplex virus 1 (HSV-1) and herpes simplex virus 2 (HSV-2). HSV1 primarily causes mouth, throat, face, eye, and central nervous system infections, while HSV2 primarily causes anogenital infections. However, each may cause infections in all areas of the body. Herpes simplex virus infection causes several distinct medical disorders. Common infection of the skin or mucosa may affect the face and mouth (orofacial herpes), genitalia (genital herpes), or hands (herpes whitlow).

Herpes viruses cycle between periods of active disease, presenting as blisters containing infectious virus particle, lasts for 2-21 days, followed by a remission period, during which the sores disappear. Genital herpes, however, is often asymptomatic, though viral shedding may still occur. In all cases herpes simplex virus is never removed from the body by the immune system. Following a primary infection, the virus enters the nerves at the site of primary infection, migrates to the cell body of the neuron, and becomes latent in the ganglion, and resides as lifelong. Causes of recurrence are uncertain, though some potential triggers have been identified. Herpes simplex is most easily transmitted by direct contact with a lesion or the body fluid of an infected individual, and may also be transmitted through skin-to-skin contact during periods of asymptomatic shedding.

A cure for herpes simplex has not yet been developed. Once infected, the virus remains in the body for life. Vaccines are in clinical trials but have not demonstrated effectiveness. There is no method to eradicate herpes virus from the body, but antiviral medications can reduce viral shedding and can reduce the frequency, duration, and severity of symptomatic episodes. There are several oral antivirals that are effective for treating herpes simplex including acyclovir, valacyclovir, famciclovir, and penciclovir. Known side effects of antiviral medicines, such as Zovirax® (acyclovir) or Famvir® (famciclovir), Valtrex® (valacyclovir, include headaches, nausea, vomiting, dizziness, abdominal pain, joint pain, confusion, depression, and cardiac irregularity. Alpha-interferon has shown synergism with other anti-HSV drugs such as caffeine, trifluorothymidine, dimethyl sulfoxide, and nonoxynol-9.

Analgesics such as ibuprofen and acetaminophen have been used to reduce pain and fever. Topical anesthetic treatments such as prilocalne, lidocaine, benzocaine or tetracaine have also been used to relieve itching and pain.

Topical antiviral agents have been used to treat herpes simplex, including acyclovir, idoxuridine in dimethyl sulfoxide, and penciclovir. It has been reported that idoxuridine reduced pain duration and decreased time to loss of crust in a study. In a study, application of penciclovir cream, both early and late in the course of HSV infection, decreased the duration of lesions, pain, and viral shedding (Hamuy R. et al, *Eur J. Dermatol.* 1998 Jul-Aug, 8(5):310-9).

Anti-inflammatory agents, often included in the topical formulations, have been used to control the inflammatory process of herpes simplex and herpes zoster. The anti-inflammatory agents include, for example, hydrocortisone, hydrocortisone acetate and dexamethasone sodium phosphate.

Varicella zoster virus is also known as chickenpox virus, varicella virus, zoster virus, and human herpes virus type 3 (HHV-3). Primary varicella zoster virus infection results in chickenpox which generally occurs in children and young people. Even when clinical symptoms of chickenpox have resolved, varicella zoster virus remains dormant in the nervous system of the infected person (virus latency), in the trigeminal and dorsal root ganglia. In about 10-20% of cases, varicella zoster virus reactivates later in life causing herpes zoster or shingles, an illness with very different symptoms. It is reported that throughout the world the incidence rate of herpes zoster every year ranges from 1.2 to 3.4 cases per 1,000 healthy individuals, increasing to 3.9-11.8 per year per 1,000 individuals among those older than 65 years.

Herpes zoster or shingles is a viral disease. Years or decades after the initial chickenpox infection, the virus may break out of nerve cell bodies and travel down nerve axons to cause viral infection of the skin in the region of the nerve. The virus may spread from one or more ganglia along nerves of an affected segment and infect the corresponding dermatome (an area of skin supplied by one spinal nerve) causing a painful rash. The earliest symptoms of herpes zoster, including headache, fever, and malaise, are nonspecific. These symptoms are commonly followed by sensations of burning pain, itching, hyperesthesia (oversensitivity), or paresthesia (tingling, pricking, or numbness). The pain may be mild to extreme in the affected dermatome, with sensations that are often described as stinging, tingling, aching, numbing or throbbing, and can be interspersed with quick stabs of agonizing pain. In most cases, after one to two days the initial phase is followed by the appearance of the characteristic skin rash. The pain and rash most commonly occurs on the torso, resulting in a stripe or belt-like pattern that is limited to one side of the body, but can appear on the face, eyes or other parts of the body. Later, the rash becomes vesicular, forming small blisters filled with a serous exudate, as the fever and general malaise continue. The painful vesicles eventually become cloudy or darkened as they fill with blood, crust over within seven to ten days, and usually the crusts fall off and the skin heals; but sometimes, after severe blistering, scarring and discolored skin remain. Although the rash usually heals within two to four weeks, some sufferers experience residual nerve pain for months or years, a condition called postherpetic neuralgia. Herpes zoster oticus is a common complication of shingles; it is a herpes zoster virus infection of the inner, middle, and external ear. Herpes zoster oticus manifests as severe otalgia and associated cutaneous vesicular eruption, usually of the external ear canal and pinna. When associated with facial paralysis, the infection is called Ramsay Hunt syndrome or Ramsay Hunt syndrome type II.

It is until recent years, two vaccines for varicella zoster virus infection, Varivax® (varicella vaccine) for children and Zostavax® (zoster vaccine) for older adults, become available. Several oral antiviral drugs have been used to treat varicella zoster virus infection, these include acyclovir for the chicken pox, famciclovir and valaciclovir for the shingles. Antiviral drug treatment can reduce the severity and duration of herpes zoster if a seven to ten day course of these drugs is started within 72 hours of the appearance of the characteristic rash. In some countries, interferon injection has been used to treat herpes zoster in recent years, however, the side effects can be adverse, particularly among older adults. Even under potent antiviral drug treatments, often the severe pain caused by the infection is unbearable to the patients.

The macrocyclic lactones (avermectins and milbemycins) are products or chemical derivatives thereof, of soil microorganisms belonging to the genus *Streptomyces*. The avermectin series and milbemycin series of compounds are very potent antiparasitic agents, useful against a broad spectrum of endoparasites and ectoparasites in mammals and also having agricultural utilities against various nematode and insect parasites found in and on crops and in soil. Compounds of this group include avermectins, milbemycins, and their semi-synthetic derivatives, for example, ivermectin, doramectin, emamectin, eprinomectin, selamectin, latidectin, milbemectin, moxidectin, nemadectin, milbemycin oxime, and lepimectin. These chemicals have been described, for example, in U.S. Pat. Nos. 3,950,360, 4,199,569, 4,879,749 and 5,268,710. The avermectins and, to a lesser extent, the milbemycins, have revolutionized antiparasitic and antipest control over the past few decades.

In terms of their mechanism of action as antiparasitic agents, the avermectins block the transmittance of electrical activity in nerves and muscle cells by activating voltage dependent membrane-bound proteins containing chloride channels. Chloride channel blockers in both insects and mammals are highly toxic convulsants causing a hyperexcitation of the nervous system through antagonism of the inhibitory neurotransmitter GABA. Avermectin compounds effectively block GABA stimulated uptake and cause a release of chloride-channel dependent neurotransmitters. Milbemycin compounds have a similar mechanism of action, but a longer half-life than the avermectins. Milbemycin compounds open glutamate sensitive chloride channels in neurons and myocytes of invertebrates, leading to hyperpolarization of these cells and blocking of signal transfer.

Ivermectin has been used as an antiparasitic agent to treat various animal parasites and parasitic diseases since mid-1980's. It is commercially available for animal use as Cardomec™ (ivermectin, for felines), Zimecterin® (ivermectin, for equines) and Ivomec® (ivermectin, for bovines) by MERIAL Limited, Duluth, Ga. The medicine is available in tablets, paste, or chewables for heartworm prevention, topical solution for ear mite treatment, or as oral or injectable solution for other parasite problems. Ivermectin is also commercially available from Merck & Co., Inc for human use under the trade name of Stromectol® (ivermectin) for eradication of threadworm Strongyloides stercoralis, and for eradication of Onchocerca volvulus. The medicine is available in tablets and is orally administered by the patients. Magda et al. (*Amer. J. Trop. Med. Hyg.* 53(6) 1995 pp. 652-653) describe a method of topical application of ivermectin to treat head lice. U.S. Pat. No. 5,952,372 (to McDaniel) discloses a method of treating a form of rosacea associated with the ectoparasite Demodex by eliminating mites.

Recently, ivermectin has also been found useful in treating dermatological conditions. U.S. Pat. Nos. 6,133,310, 6,433,006, 6,399,652, 6,399,651 and 6,319,945 (to Parks) disclose methods of treating acne rosacea, seborrheic dermatitis, acne vulgaris, transient acantholytic dermatitis, acne miliaris necrotica, acne varioliformis, perioral dermatitis, and acneiform eruptions by topically applying an avermectin compound, particularly ivermectin, to the affected areas.

The above described parasitic diseases and dermatological conditions are not viral diseases and have different etiologies from herpes simplex virus and varicella zoster virus infections.

Herpes simplex is common public health problem. It has been reported recently that herpes simplex virus infection affects approximately 60% to 95% of adults worldwide. On the other hand, topical treatment for the painful symptoms of herpes zoster is limited. Therefore, there is a need for more effective and better topical treatments for treating herpes simplex virus and varicella zoster virus infections.

SUMMARY OF THE INVENTION

In one embodiment, the present invention is directed to a method of treating herpes simplex virus infection or varicella zoster virus infection comprising topically applying a composition comprising an effective amount of one or more macrocyclic lactone compounds including avermectin compounds, milbemycin compounds or mixture thereof and a pharmaceutically acceptable carrier to an affected area of an individual suffering from herpes simplex virus infection or varicella zoster virus infection. The virus infections are herpes simplex, herpes zoster or shingles, or chickenpox.

In another embodiment, the present invention is directed to a composition comprising one or more avermectin compounds or milbemycin compounds or mixture thereof for treating herpes virus infection including herpes simplex virus infection or varicella zoster virus infection.

The avermectin compounds in the composition include avermectins, or avermectin derivatives such as ivermectin, ivermectin derivatives, emamectin, doramectin, selamectin, eprinomectin, or latidectin. The milbemycin compounds include milbemycins, or milbemycin derivatives such as moxidectin, nemadectin, milbemycin oxime, or lepimectin. Preferably, the composition comprises an effective amount of ivermectin.

The advantages of the present invention will become apparent from the following description in conjunction with exemplary embodiments of the invention.

DETAILED DESCRIPTION OF THE INVENTION

In one embodiment, the present invention provides a method of treating herpes simplex virus infection or varicella zoster virus infection using one or more macrocyclic lactone compounds. In one embodiment, the method comprises topically applying a composition comprising an effective amount of one or more one or more macrocyclic lactone compounds including avermectin compounds, milbemycin compounds, or mixture thereof, and a pharmaceutically acceptable carrier to an affected area of an individual suffering from herpes simplex virus infection or varicella zoster virus infection.

In another embodiment, the present invention provides the use of one or more macrocyclic lactone compounds including avermectin compounds, milbemycin compounds, or mixture thereof in the preparation of a pharmaceutical composition intended for the treatment of herpes simplex virus infection or varicella zoster virus infection. Unless defined otherwise, all technical and scientific terms used herein have the same meaning as commonly understood by one having ordinary skills in the art to which the invention belongs.

The herpes simplex virus infection herein refers to the infection caused by herpes simplex virus-1, herpes simplex virus-2, or both, at any area of the body. The viral disease herein is generally referred to as herpes simplex, which includes, but not limited to, orofacial herpes including herpetic gingivostomatitis and herpes labialis (colloquially called cold sores or fever blisters), herpes genitalis (commonly known simply as herpes), herpetic whitlow, herpes gladiatorum, and herpetic sycosis. The varicella zoster virus infection herein refers to the infection caused by human herpes virus-3, which includes herpes zoster (more commonly known as shingles), including herpes zoster oticus, and chickenpox.

The macrocyclic lactone compounds for the purpose of the present invention include avermectin compounds and milbemycin compounds. The avermectin compounds for the purpose of the present invention include avermectins and derivatives thereof, which include, but not limited to, avermectin $A_{1a}$, $A_{1b}$, $A_{2a}$, $A_{2b}$, $B_{1a}$, $B_{1b}$, $B_{2a}$ and $B_{2b}$, ivermectin and derivatives thereof, emamectin, doramectin, selamectin, eprinomectin, latidectin, or mixtures thereof. The milbemycin compounds for the purpose of the present invention include milbemycins and derivatives thereof, which include, but not limited to, milbemycins, moxidectin, nemadectin, milbemycin oxime, milbemectin, lepimectin, or mixtures thereof.

In one embodiment, the composition comprises one or more avermectin compounds and a pharmaceutically acceptable carrier or a medium which is suitable for application to the affected area of herpes simplex virus or varicella zoster virus infection, as described further in detail hereinafter. In another embodiment, the composition comprises one or more milbemycin compounds and a pharmaceutically acceptable carrier or a medium which is suitable for application to the affected area of herpes simplex virus or varicella zoster virus infection, as described further in detail hereinafter. Preferably, ivermectin is used in the composition.

The following molecular structure represents the avermectin series of compounds, which can also be chemically converted to useful derivatives as discussed below.

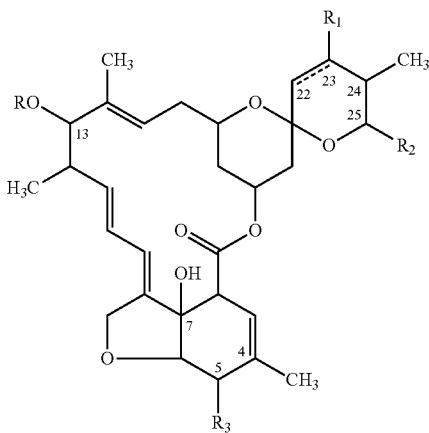

wherein the broken line at the 22-23 position represents an optional double bond; $R_1$ is hydroxy and is present only when the bond at the 22-23 position is a single bond; $R_2$ is isopropyl or sec-butyl; $R_3$ is methoxy or hydroxyl, and R is the 4'-(alpha-L-oleandrosyl)-alpha-L-oleandroside of the structure:

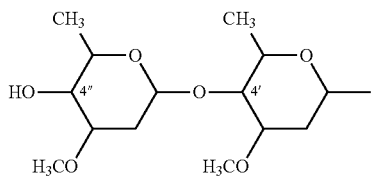 [SMILES: COC1CC(OC2C(C)OC(C)CC2OC)OC(C)C1O]

The naturally occurring avermectins are a series of 16-membered macrocyclic lactones isolated from fermentation products of Streptomyces avermitilis, a soil Actinomycete. There are eight different but closely related compounds produced by Streptomyces avermitillis, isolated in four pairs of homologue compounds with a major (a-component) and minor (b-component) component, which are designated as avermectin $A_{1a}$, $A_{1b}$, $A_{2a}$, $A_{2b}$, $B_{1a}$, $B_{1b}$, $B_{2a}$, and $B_{2b}$. The mixture of avermectin $B_{1a}$ and $B_{1b}$, widely used insecticide and antihelmintic, are commonly referred to as abamectin. The production of these compounds is described in U.S. Pat. No. 4,310,519, which is incorporated herein by reference in its entirety. The structures of these eight individual compounds in reference to the above structural formula have been identified as follows:

|          | $R_1$       | $R_2$      | $R_3$   |
|----------|-------------|------------|---------|
| $A_{1a}$ | Double bond | sec-butyl  | —$OCH_3$ |
| $A_{1b}$ | Double bond | iso-propyl | —$OCH_3$ |
| $A_{2a}$ | —OH         | sec-butyl  | —$OCH_3$ |
| $A_{2b}$ | —OH         | iso-propyl | —$OCH_3$ |
| $B_{1a}$ | Double bond | sec-butyl  | —OH     |
| $B_{1b}$ | Double bond | iso-propyl | —OH     |
| $B_{2a}$ | —OH         | sec-butyl  | —OH     |
| $B_{2b}$ | —OH         | iso-propyl | —OH     |

The 22, 23-double bond of some avermectins may be selectively reduced to prepare ivermectin and its derivatives. Ivermectin, a member of avermectin compound family, is a semi-synthetic derivative of avermectin and is generally produced as a mixture of 22,23-dihydroavermectin $B_{1a}$ and 22,23-dihydroavermectin $B_{1b}$. The preparation of ivermectin and derivatives are disclosed in U.S. Pat. No. 4,199,569, which is incorporated herein by reference in its entirety.

The following structural formula shows the structures of ivermectin and its derivatives:

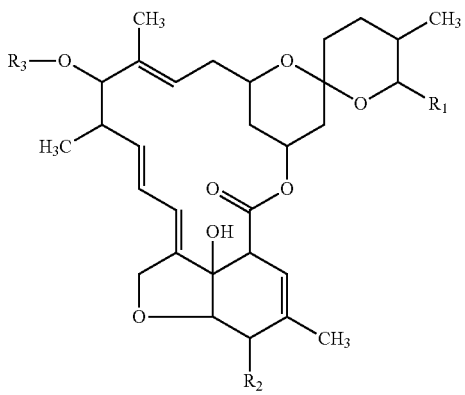

wherein $R_1$ is iso-propyl or sec-butyl; $R_2$ is methoxy, hydroxy or alkanoyloxy; $R_3$ is hydrogen; alkanoyl; alpha-L-oleandrosyl; 4'-alkanoyl-alpha-L-oleandrosyl; 4'-(alpha-L-oleandrosyl)-alpha-L-oleandrosyl; or 4"-alkanoyl-4'-(alpha-L-oleandrosyl)-alpha-L-oleandrosyl. Herein, the "alkanoyl"

includes alkanoyl groups having 2 to 6 carbon atoms such as acetyl, propionyl, butyryl, and pivaloyl. Ivermectin and its derivatives shown above share profound anthelmintic, insecticidal, ectoparasiticidal and acaricidal activity.

Doramectin and eprinomectin are represented by the following structure:

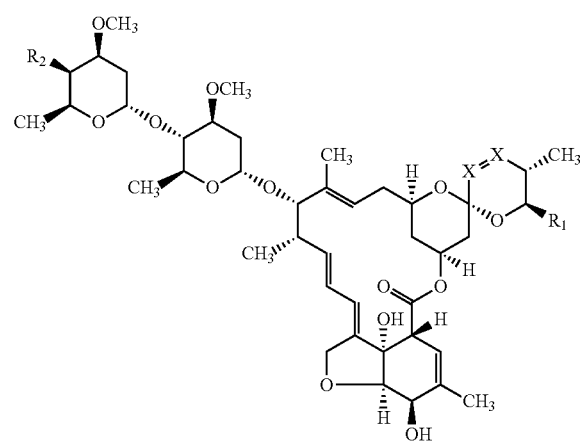

In doramectin, x=x is —CH=CH—, $R_1$ is —$C_6H_{10}$, $R_2$ is —OH. In eprinomectin, x=x is —CH=CH—; $R_1$ is —CH($CH_3$)$CH_2CH_3$, or —CH($CH_3$)$_2$; $R_2$ is —NHCOCH$_3$. These compounds are described in "Veterinary Parasitology", vol. 49, No. 1, July 1993, 5-15.

Selamectin has the following structure:

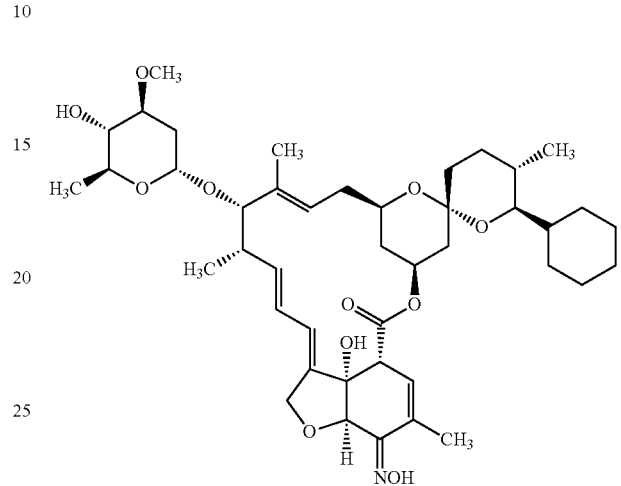

which is described in EP1142577A2 and WO 94/15944.

Emamectin has the following structure:

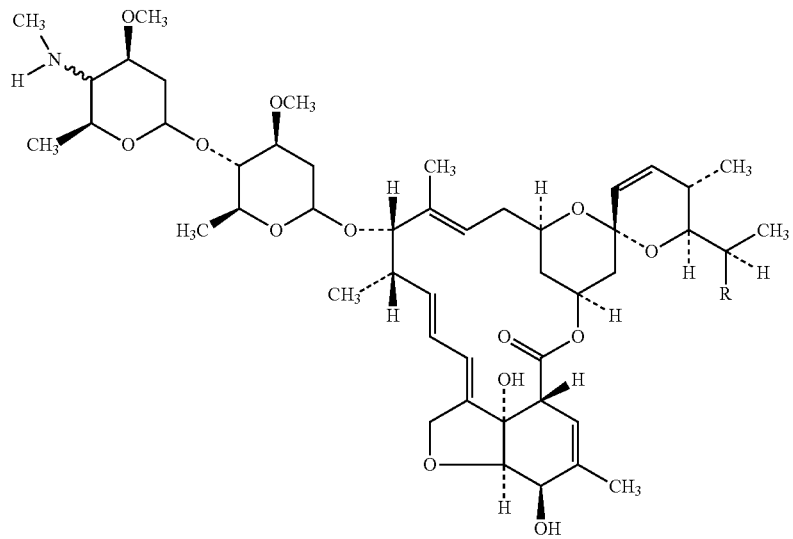

where R is —CH₂CH₂ or —CH₃. Emamectin and its salts are described in U.S. Pat. No. 4,874,749.

The structure of latidectin, which is a mixture of components A3 and A4, is shown below:

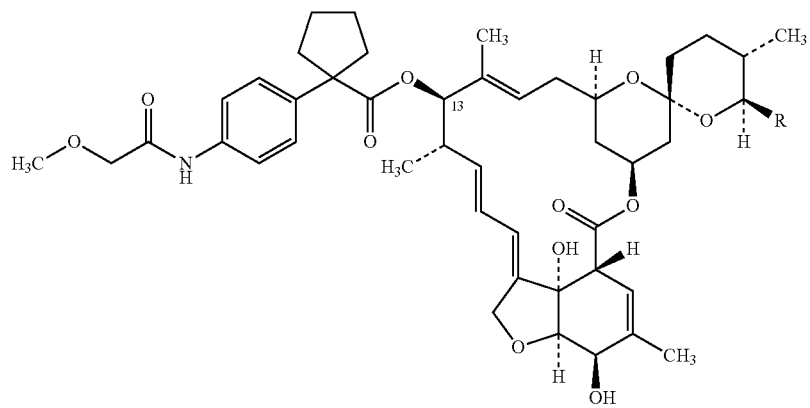

where component A3 has R═—CH₂CH₃, and component A4 has R═—CH₃.

Other avermectin derivatives are also known in the art. For example, the avermectins possess a disaccharide moiety at the C-13 position consisting of the alpha-L-oleandrosyl-alpha-L-oleandrosyl group. One or both of these saccharide groups may be removed as described in U.S. Pat. No. 4,206,205; and the produced aglycone derivatives have a hydroxy group at the 13-position. This group may be removed to form the 13-deoxy compound as described in U.S. Pat. Nos. 4,171,314 and 4,173,571, and the latter patent also describes the 13-halo derivatives. U.S. Pat. No. 5,077,308 describes avermectin aglycone derivatives which incorporate a ketal at C-13 position. The avermectins and derivatives have several hydroxy groups which may be acylated as described in U.S. Pat. No. 4,201,861. U.S. Pat. No. 5,055,454 describes avermectin derivatives in which position 13 of avermectin has been inverted from a normal alpha stereochemistry to the epimeric C-13 beta stereochemistry. U.S. Pat. No. 5,162,363 describes avermectin derivatives where the 23-position ring carbon atom is replaced with sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All aforementioned patents are incorporated herein by reference in their entirety.

All avermectin compounds mentioned above share the 16-membered macrocyclic lactone ring and the spectrum of anti-parasitic biological activity of ivermectin, varying only in degree. It is expected that they also share the activity spectrum of ivermectin suitable for the purpose of the present invention.

Like avermectins, milbemycins are products of fermentation by *Streptomyces* species, isolated from the fermentation broth of *Streptomyces hygroscopicus* subsp. *aureolacrimosus*. They have same mode of action, but a longer half-life than the avermectins. Milbemycins include α series and β series, which were initially named as B-41 antibiotics and given the designation $A_1, A_2, A_3, A_4, B_1, B_2, B_3, C_1$ and $C_2$, as described in U.S. Pat. Nos. 3,950,360 and 3,984,564. The B-41 designations are still commonly used today. The correlation of the initial designation to the nomenclature of α and β series of some milbemycins is described in U.S. Pat. No. 4,144,352. Within the family, milbemycins $\alpha_{11}, \alpha_{14}, A_3$ and $A_4$ have been found having the most effective acaricidal activity. A mixture of milbemycins $A_3$ and $A_4$ is commercialized under the name milbemectin.

The following structural formula represents milbemectin and several potent derivatives of milbemycins:

| | R₁ | R₂ | R₃ |
|---|---|---|---|
| Milbemectin | —H, (β)—OH | —H, —H | —CH₃; —CH₂CH₃ |
| Milbemycin oxime | ═NOH | —H, —H | —CH₃; —CH₂CH₃ |
| Moxidectin | —H, (β)—OH | ═NOCH₃ | (Z)—C(CH₃)═CH—CH(CH₃)₂ |
| Nemadectin | —H, (β)—OH | —H, (α)—OH | (Z)—C(CH₃)═CH—CH(CH₃)₂ |

Further description of milbemycins and their derivatives can be found in "Avermectins and Milbemycins", Davies H. G. et al., 1986, Nat. Prod. Rep., 3, 87-121; "Synthesis of Milbemycins from Avermectins", Mrozik H. et al., 1983, Tetrahedron Lett., 24, 5333-5336; and U.S. Pat. Nos. 4,134,973 and 4,144,352.

A further derivative of milbemycin is lepimectin, which has the following structure:

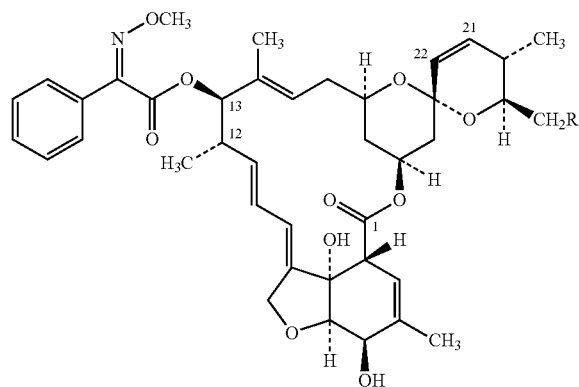

where R is —CH$_2$CH$_3$ (major component), and R is —CH$_3$ (minor component).

Both avermectins and milbemycins have macrocyclic lactone structures that are superimposable, they are produced by the same genus of soil dwelling organisms, they have the same mode of action, and they exert this action against the same nematode/acarine/insect spectrum of targets. It is expected that milbemycin compounds also share the activity spectrum of ivermectin suitable for the purpose of the present invention.

The concentration of the one or more avermectin compounds or the one or more milbemycin compounds in the composition for the purpose of the present invention can be greater than 0.001% weight by weight (w/w). In some embodiments, the concentration of the one or more avermectin compounds or the one or more milbemycin compounds in the composition is in a range from about 0.001% to about 10% (w/w), preferably from about 0.03% to about 5% (w/w), and more preferably from about 0.05% to about 3% (w/w). In a preferred embodiment, ivermectin is used. The concentration of ivermectin in the composition can be greater than 0.001% (w/w). In some embodiments, the concentration of ivermectin in the composition is from about 0.001% to about 10% (w/w), preferably from about 0.03% to about 5% (w/w), and more preferably from about 0.05% to about 3% (w/w). In one embodiment, the composition is a topical composition. It has been found that a topical composition containing ivermectin at a concentration as low as 0.075% is effective, as illustrated in the examples hereinafter, in treating herpes simplex and herpes zoster. Such a low effective concentration is advantageous because it reduces risks of side effects and the possibility of triggering body's autoimmune responses.

The composition can be in various forms, including, but not limited to, solution, spray, gel, ointment, or emulsion in the form of liquid suspension, lotion, or cream. The composition can also be integrated into or applied on dermal patch, medical tape, medical dressing, or lint free wipes, which can be applied on the affected area as needed, to provide an extended exposure of the skin to the medication. Furthermore, the composition can also be in the form of suspensions of microspheres or nanospheres, lipid or polymeric vesicles, or polymeric patches or hydrogels for controlled release.

Pharmaceutically acceptable carriers or media suitable for topical application are known to those skilled in the art. In some embodiments, a topical composition is provided, which comprises one or more surfactants that enhance penetration of the active component avermectin compound into the skin. As described above, herpes simplex virus and varicella zoster virus cause viral infections of the skin in the region of the nerve. Therefore, to effectively treat inflammation caused by the virus infection it is important to have the active component of the topical composition penetrated or delivered into the skin. Surfactants are usually organic compounds that are amphiphilic, containing both hydrophobic or lipophilic tail groups and hydrophilic head groups. Surfactants may act as wetting agents, emulsifiers, foaming agents, and dispersants. Surfactant molecules form vesicles and/or micelles, which disperse the macrocyclic lactone compound in an aqueous medium. Moreover, when applied topically the surfactants wet the surface of the skin upon contact and enhance penetration and delivery of the dispersed macrocyclic lactone compound in the composition into the skin. The surfactants can be anionic, cationic, non-ionic, zwitterionic surfactants, or combinations thereof.

Other known dermal penetrating agents can also be used for the purpose of the present invention. Suitable examples may include medium used in dermal patches for drug or hormone delivery, with or without controlled release.

In one exemplary embodiment, the topical composition is in a form of lotion having substantially neutral pH from about 6 to about 7. Example 1 provides an exemplary topical composition comprising ivermectin in a lotion. As shown in the example, a commercially available moisturizing lotion manufactured by Galderma Laboratories, Inc. under the trade name Cetaphil® moisturizing lotion is used as the medium for ivermectin to form the topical composition. Cetaphil® moisturizing lotion contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, and citric acid.

In some embodiments, the composition is an emulsion with one or more macrocyclic lactone compound therein. More specifically, the topical composition comprises one or more avermectin compound or milbemycin compound, one or more solvents for the active agent, an oily phase, one or more surfactants as emulsifier, and water. The method of preparing an emulsion is known to those skilled in the art. The emulsion can be formulated into a solution, lotion, or cream. The emulsion can also be sprayable. Example 2 provides an exemplary topical composition, which is a cream containing 1% of ivermectin.

The topical composition in the form of ointments can be prepared using either an oleaginous base or medium or an absorbent base. The oleaginous base comprises fixed oils or hydrocarbons, such as white petrolatum or mineral oil. The absorbent base comprises an anhydrous substance or substances which can absorb water, for example anhydrous lanolin. Following formation of the base, the macrocyclic lactone compound is added to an amount affording the desired concentration to form the topical composition.

The topical composition in the form of gel can comprise an oleaginous medium, water, or an emulsion medium described above. One or more gelling agents are added into the medium, which forms a matrix therein and increases the viscosity of the medium. Typically, the avermectin compound is added to the formulation at the desired concentration at a point preceding addition of the gelling agent.

Furthermore, the topical composition of the present invention can be in the form of hydrogels or thermal responsive hydrogels suitable for delivering the active component across the skin. Upon applying to the affected area, the thermal responsive hydrogel can change from a liquid suspension to gel upon exposure to the body temperature and forms a coating on the skin. The adhesion to the surface can facilitate penetration and effective delivery of the active component across the skin.

The composition of the present invention described above is applied to the affected area of patients having herpes simplex, herpes zoster, or chicken-pox. Preferably, the lotion, cream, gel, or ointment can be applied on the affected area with gentle rubbing to help penetration of the macrocyclic lactone compound into the skin. Moreover, when lotion, cream, or hydrogel is used, preferably the affected area is dampened by water first, then a drop of lotion, cream, or hydrogel is rubbed on the affected area by finger(s). It has been found that dampened skin is more absorbent to the medication, hence, wetting the surface first may further facilitate absorption and penetration of the macrocyclic lactone compound into the skin. Moreover, if blisters are already formed at the affected area, at the time of applying the topical composition the blisters can be broken using a needle, then the composition is rubbed in the lesion. It has been found that introducing the composition into lesion allows more effective penetration of ivermectin and enhances the effectiveness of the treatment.

For treating herpes zoster, preferably the surface of the affected area of the skin is gently scratched prior to rubbing the composition containing the macrocyclic lactone compound on the area. Gentle scratching abrades the stratumcorium, which allows better penetration of the macrocyclic lactone compound into the skin. The stratum corneum is the outermost layer of the epidermis, composed of large, polyhedral, plate-like envelopes filled with keratin, which is made up of dead cells that have migrated up from the stratum granulosum. As these dead cells slough off on the surface, they are continuously replaced by new cells from the stratum germinativum. Alternatively, the composition can be dispensed on the affected area, and then scratched into the area. Scratching with cleaned finger nails or a sterilized scraping tool, for example small sharp curette or a needle point, can be used.

The composition can be applied topically to the affected area one or more times a day, typically one to two times a day, when a herpes simplex episode occurs or during the course of shingles or chicken box. When the pain is severe, the composition can be applied more frequently to help alleviate the symptoms. Moreover, the composition can also be integrated into or applied on medical dressing, dermal patch, or lint free wipes, which can be applied to the affected area as needed, to provide a more extended exposure to the medication.

It has been discovered by the inventors that topical application of the composition containing ivermectin is effective in treating herpes simplex virus infection and varicella zoster virus infection, particularly at early onset of the conditions. Examples 3 through 8 illustrate the effectiveness of the method of the present invention in treating herpes simplex virus infection and varicella zoster virus infection.

For treating the herpes simplex, it has been found that the results have been consistently excellent. The most impressive results are seen with early recognition and treatment. However, even in older lesions the topical treatment using the ivermectin lotion speeds the rate of healing. If the patient is astute to recognize the prodrome of these blistering eruptions and promptly applies the ivermectin lotion to the affected area, the blister formation is either attenuated or abated entirely. In medicine, a prodrome is an early symptom (or set of symptoms) that might indicate the start of a disease before specific symptoms occur. Prodromes may be non-specific symptoms or, in some instances, may clearly indicate a particular disease. In herpes simplex there is a prodrome consisting of a change in sensation, typically slight numbness or a faint tingling sensation with vague swelling or induration. It has been found that at this point if the patient dampens the skin with water and then rubs a drop of the ivermectin lotion containing about 0.075% to about 0.1% ivermectin (as shown in Example 1), in most cases the lesion heals in 24 to 48 hours without forming a vesicle.

For herpes zoster, at the early onset the patient develops a patch of linear area of paresthesia, and hyperesthesia (burning, stinging, and pain). At this time, the composition containing ivermectin should be topically applied promptly and scratched into the skin. Concurrently, an oral antiviral medication can be used promptly. The combined systematic and topical treatments have a synergistic effect in decreasing the severity of this potentially disabling disorder. It has been found that using a combined systematic antiviral treatment and the topical treatment of the present invention, a better result is obtained in treating herpes zoster.

Although the applicants are not bound by any theoretical explanation as to why the composition and the method of the present invention are effective in treating herpes simplex virus and varicella zoster virus infections, presentation of certain theoretical understanding may be of value. Based on clinical observations by the inventors, it is believed that the efficacy of the composition and the method of the present invention in topical treatment of herpes simplex virus and varicella zoster virus infections is due in part to the anti-inflammatory property of ivermectin, and its antiseptic properties. It is believed that ivermectin is an effective anti-inflammatory agent, which blocks certain mediators of inflammation, therefore, diminishes symptoms caused by inflammation. Moreover, in view of the effect of ivermectin on neural system, it may also have some direct effects on the neural receptors in the skin, which may contribute to the significant pain relief observed clinically.

The composition containing ivermectin can be provided as a kit wherein the composition is packaged in a container. Instructions on how to use the composition in accordance with the present invention are included on or associated with the container, which provides detailed instructions for treating herpes simplex virus infection and/or varicella zoster virus infection. Optionally, the kit further includes one or more tools to facilitate scratching, such as curette.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Composition A of an ivermectin lotion is prepared as follows: mix 0.04 g of Zimecterin® (ivermectin, manufactured by MERIAL Limited, Duluth, Ga.) which contains 1.87% ivermectin, sufficiently with 100 mg of Cetaphil® moisturizing lotion (manufactured by Galderma Laboratories, Inc.) to form an ivermectin lotion. The ivermectin concentration in the formed lotion is 0.075% (w/w).

Composition B of an ivermectin lotion is prepared as follows: mix 0.054 g of Zimecterin® (ivermectin) containing 1.87% ivermectin sufficiently with 100 mg of Cetaphil® moisturizing lotion to form an ivermectin lotion. The ivermectin concentration in the formed lotion is 0.1% (w/w).

Other suitable compositions that can be made in accordance with Example 1 include ivermectin in the following concentrations: 0.01%, 0.05%, 0.12%, 0.15%, 0.2%, 0.5%, 1% and 2% (w/w) with Cetaphil® moisturizing lotion as a medium. Other compatible commercial available lotions can also be used as a medium or carrier.

EXAMPLE 2

The following emulsion is prepared with the method known in the art.

| Ingredients | Percentage (% w/w) |
| --- | --- |
| Ivermectin | 1.0 |
| Glycerol | 4.0 |
| Acrylate C10-30 alkyl acrylate crosspolymer | 0.2 |
| Methyl para-hydroxybenzoate | 0.2 |
| Disodium EDTA | 0.05 |
| Citric acid monohydrate | 0.05 |
| Isopropyl palmitate | 4.0 |
| Cetyl alcohol | 3.5 |
| Stearyl alcohol | 2.5 |
| Oleyl alcohol | 2.0 |
| Ceteareth-20 | 3.0 |
| Sorbitan monostearate | 2.0 |
| Dimethicone 200 20 cs | 0.5 |
| Propyl para-hydroxybenzoate | 0.1 |
| Propylene glycol | 2.0 |
| Phenoxyethanol | 1.0 |
| 10% sodium hydroxide | qs pH to 6.3 |
| Water | qs 100 |

The emulsion prepared is in the form of cream.

Operating with informed consent of individuals, individuals were treated with the topical composition and the method of the present invention for treating herpes virus infection, more particularly herpes simplex and herpes zoster or shingles, as described in Examples 3 to 8.

EXAMPLE 3

A 64-year old retired male physician with a multi-year history of herpes simplex Of the lips, perioral areas, and occasionally, intraoral areas. Prior therapy included Zovirax® (acyclovir, orally) with benefit and topically without benefit. The patient was given Composition A of the ivermectin lotion of Example 1 to use topically twice a day at the first sign or prodrome that an eruption was imminent. This resulted in the prompt aborting of a full blown blistering lesion, and also a decrease in the healing time for lesions that had vesicated. Over more than two years of consistent early applications of the ivermectin lotion, the patient has reported that the incidence of recurrent lesions has diminished dramatically.

EXAMPLE 4

A 38-year old female presented with a history of recurrent episodes of herpes labialis. Prior therapies had been unsatisfactory from the standpoint of response and cost. A sample of Composition A of the ivermectin lotion of Example 1 was provided to the patient to be applied topically to the affected area of the lips twice a day at the first sign of an eruption or of an impending eruption. The patient found that the herpes labialis responded well to the topical treatment with the ivermectin lotion, but without the high cost of Zovirax® (acyclovir) or Famvir® (famciclovir).

EXAMPLE 5

A 43 year-old female with a multiyear history of herpes affecting multiple areas of the body, including hips, thighs, face, and other areas. The patient had been on numerous different therapies including high dose of Valtrex® (valacyclovir), all without total satisfaction. Moreover, the use of Valtrex® (valacyclovir) had caused her cardiac irregularities, especially bigeminy and trigeminy. A sample of Composition A of the ivermectin lotion of Example 1 was provided to the patient to be applied topically to the affected area twice a day. For more than two years of trial, the patient has reported that the topical treatment with the ivermectin lotion has had as good or better result than the other modalities, but without the side effects and high cost of Valtrex® (valacyclovir).

Numerous other patients have been treated using Composition A or B of the ivermectin lotion and the method of the present invention. All have demonstrated a good to excellent response to the ivermectin lotion for control of their herpes simplex.

EXAMPLE 6

A 63 year-old male presented with a five day history of shingles in a band on the skin of his left thorax at the level of T-8 and 9. The patient had severe pain with burning and tingling that had not responded to high dose of Famvir® (famciclovir). The patient was then treated with Composition A of the ivermectin lotion of Example 1 one to two times a day. All persistent vesicles and pustules were decapitated first to allow penetration of the lotion into the lesions, and then the ivermectin lotion is rubbed on the affected area. This afforded immediate relief of the severe pain and the steady healing of the damaged skin.

EXAMPLE 7

A 50-year old white male presented with a patch of vesicles on the left scapula. The patient was given Famvir® (famciclovir) 1000 mg three times a day and Composition A of the ivermectin lotion of Example 1 for topical application to the affected area twice a day, after breaking all blisters to improve penetration. Using the oral and topic treatments, the patient's progress was steady and was mostly healed in three weeks. No post herpetic neuralgia developed.

EXAMPLE 8

A 85-year old female with a four day history of shingles, involving the left neck, ear, shoulder and upper chest, had been treated with Famvir® (famciclovir) 1000 mg three times a day and topical Zovirax® (acyclovir) ointment. The lesions were beginning to dry and crust; however, the skin was still tender with burning, stinging pain. The Composition B of the ivermectin lotion of Example 1 was topically applied to the affected area. Ten minutes after applying the ivermectin lotion, she remarked "My, the lotion was certainly cooling, soothing and abating the skin pain". The ivermectin lotion was subsequently used twice a day. The patient continued to steadily improve and heal without post herpetic neuralgia.

In the above described informal trials, no adverse side effects or contra-indications were observed among the patients. The patients had no complaints of skin irritation, sensitivity or discomfort originating from the treatment.

Each patent, patent application, publication, text and literature article or report cited or indicated herein is hereby expressly incorporated by reference in its entirety.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method of treating herpes virus infection comprising locally applying an effective amount of one or more macrocyclic lactone compound to an affected area of an individual suffering from herpes simplex virus infection or varicella zoster virus infection, wherein said macrocyclic lactone compound is avermectin compound, milbemycin compound, or mixtures thereof.

2. The method of claim 1, wherein said virus infection is caused by herpes simplex virus-1, herpes simplex virus-2, or varicella zoster virus.

3. The method of claim 1, wherein said virus infection is herpes simplex herpes zoster (or shingles), or chickenpox.

4. The method of claim 1, wherein said method comprises topically applying said macrocyclic lactone compound on the affected area associated with herpes simplex, herpes zoster, or chickenpox.

5. The method of claim 1, wherein said method comprises topically applying said macrocyclic lactone compound on a lesion associated with herpes simplex, herpes zoster or chickenpox.

6. The method of claim 1, wherein said method comprises applying said macrocyclic lactone compound into blisters associated with herpes simplex, herpes zoster or chickenpox.

7. The method of claim 1, wherein said locally applying said macrocyclic lactone compound to the affected area includes scratching the surface of the skin of the affected area associated with herpes zoster, prior to or during application of said avermectin compound or said milbemycin compound.

8. The method of claim 1, wherein said method further comprises dampening the affected area by water first, then rubbing said macrocyclic lactone compound on the affected area.

9. The method of claim 1, wherein said macrocyclic lactone compound is applied one or more times a day to the affected area.

10. The method of claim 1, wherein said macrocyclic lactone compound is applied to said affected area at early onset of herpes simplex.

11. The method of claim 1, wherein said avermectin compound is selected from the group consisting of avermectins ivermectin, emamectin, doramectin, selamectin, eprinomectin, and latidectin.

12. The method of claim 1, wherein said milbemycin compound is selected from the group consisting of milbemycins moxidectin, nemadectin, milbemycin oxime, milbemectin, and lepimectin.

13. The method of claim 1, wherein said macrocyclic lactone compound is from about 0.001% to about 10% (w/w) in a composition.

14. The method of claim 1, wherein said avermectin compound is ivermectin.

15. The method of claim 14, wherein said ivermectin is greater than 0.001% (w/w) in a composition.

16. The method of claim 14, wherein said ivermectin is from about 0.001% to about 10% (w/w) in a composition.

17. The method of claim 1, wherein said macrocyclic lactone compound is in a lotion, cream, gel, solution, ointment, or spray.

18. The method of claim 1, wherein said macrocyclic lactone compound is integrated in a medical dressing or wipes.

19. The method of claim 1, wherein applying said macrocyclic lactone compound to the affected area attenuates and abates blister formation, and/or decreases healing time of a lesion.

20. The method of claim 1, wherein applying said macrocyclic lactone compound to the affected area rapidly relieves severe pain caused by the varicella zoster virus infection.

21. The method of claim 1, wherein at a first sign or prodrome that an eruption is imminent, applying said macrocyclic lactone compound to the affected area attenuates or abates entirely blister formation.

22. The method of claim 1, wherein said virus infection is orofacial herpes, herpetic gingivostomatitis, herpes labialis, herpes gen italis, herpetic whitlow, herpes gladiatorum, or herpetic sycosis.

23. The method of claim 1, wherein said virus infection is herpes zoster oticus.

* * * * *

UNITED STATES PATENT AND TRADEMARK OFFICE
CERTIFICATE OF CORRECTION

| | |
|---|---|
| PATENT NO. | : 8,901,091 B2 |
| APPLICATION NO. | : 13/823387 |
| DATED | : December 2, 2014 |
| INVENTOR(S) | : L. Dean Parks et al. |

It is certified that error appears in the above-identified patent and that said Letters Patent is hereby corrected as shown below:

In the Claims

Column 17, line 17, change "herpes simplex herpes zoster" to --herpes simplex, herpes zoster--

Column 18, line 6, change "milbemycins" to --milbemycins,--

Column 18, line 38, change "herpes gen italis" to --herpes genitalis--

Signed and Sealed this
Thirty-first Day of March, 2015

Michelle K. Lee
*Director of the United States Patent and Trademark Office*